United States Patent [19]

Mott

[11] Patent Number: 4,607,125

[45] Date of Patent: Aug. 19, 1986

[54] PROCESS FOR PRODUCING HYDROXY AROMATIC KETONES

[75] Inventor: Graham N. Mott, Corpus Christi, Tex.

[73] Assignee: Celanese Corporation, New York, N.Y.

[21] Appl. No.: 721,007

[22] Filed: Apr. 8, 1985

[51] Int. Cl.⁴ .............................................. C07C 45/46
[52] U.S. Cl. ..................................................... 568/319
[58] Field of Search ................................ 568/319, 327

[56] References Cited

U.S. PATENT DOCUMENTS

| | | | |
|---|---|---|---|
| 3,403,183 | 9/1968 | Dobratz et al. | 568/319 |
| 4,082,807 | 4/1978 | Eiglmeier | 568/319 |
| 4,453,010 | 6/1984 | Staniland | 568/322 |
| 4,454,350 | 6/1984 | Desbois | 568/322 |
| 4,474,990 | 10/1974 | Jansons | 568/319 |

*Primary Examiner*—James H. Reamer
*Attorney, Agent, or Firm*—M. Turken; D. R. Cassady

[57] ABSTRACT

A process of acylating a monocyclic phenolic reactant, e.g. phenol to a hydroxy aromatic ketone, e.g. 4-hydroxyacetophenone, by contacting the phenolic reactant with about 0.4 to 0.8 moles of a carboxylic acid anhydride, e.g. acetic anhydride as acylating agent per mole of phenolic reactant of in the presence of a Friedel-Crafts catalyst, e.g. hydrogen fluoride. The process generally results in phenolic reactant conversions of at least about 80% and reaction selectivities to hydroxy aromatic ketone of at least about 70%.

9 Claims, No Drawings

PROCESS FOR PRODUCING HYDROXY AROMATIC KETONES

This invention relates to a process for producing hydroxy aromatic ketones such as 4-hydroxyacetophenone.

BACKGROUND OF THE INVENTION

Hydroxy aromatic ketones such as 4-hydroxyacetophenone (4-HAP) are possible intermediates for a variety of products having a multiplicity of end uses. Thus, pending U.S. application Ser. No. 06/618,659, filed June 8, 1984, discloses a process for using hydroxy aromatic ketones, such as 4-HAP to make N-acyl hydroxy aromatic amines such as N-acetyl-para-aminophenol (APAP), better known as acetaminophen, which has wide use as an analgesic. Pending U.S. application Ser. No. 06/627,382, filed July 3, 1984, discloses the use of hydroxy aromatic ketones such as 4-HAP as an intermediate for the production of N-acyl-acyloxy aromatic amines such as 4-acetoxyacetanilide (4-AAA) which can be used for the preparation of poly(esteramide)s capable of forming an anisotropic melt phase and suitable for being formed into shaped articles such as moldings, fibers and films. In addition, 4-AAA may also be hydrolyzed to form APAP. Pending U.S. application Ser. No 06/633,832, filed July 24, 1984, discloses a process wherein hydroxy aromatic ketones such as 4-HAP are used to produce acyloxy aromatic carboxylic acids such as 4-acetoxybenzoic acid (4-ABA) which are also capable of being used directly to make polymers which can be formed into an anisotropic melt suitable for the formation of shaped articles. Moreover, 4-ABA can be hydrolyzed to 4-hydroxybenzoic acid (4-HBA) which can be used as an intermediate for the production of preservatives, dyes, and fungicides. Pending U.S. applications Ser. No. 06/661,552, filed Oct. 17, 1984, and Ser. No. 06/689,533, filed Jan. 7, 1985, disclose processes wherein hydroxy aromatic ketones such as 4-HAP are used as intermediates for the production of aromatic diols such as hydroquinone (HQ) which have utility as photographic developers, polymerization inhibitors, dye intermediates, and anti-oxidants.

Dann and Mylius in a dissertation included as part of a series of Reports from the Institute for Applied Chemistry of the University of Erlangen, received for publication on Jan. 7, 1954 and published in Annalen der Chemie 587 Band, pages 1 to 15, disclose the reaction of phenol and glacial acetic acid in the presence of hydrogen fluoride to produce 4-hydroxyacetophenone (4-HAP) in a yield of 61.6%. This reaction may be conventionally characterized as a Friedel-Crafts acetylation of phenol with acetic acid as the acetylating agent.

Simons et al, Journal of the American Chemical Society, 61, 1795 and 1796 (1939) teach the acylation of aromatic compounds using hydrogen fluoride as a condensing agent and in Table 1 on page 1796 show the acetylation of phenol with acetic acid to produce p-hydroxyacetophenone (4-HAP) in 40% yield.

European Patent Publication No. 69,597, published Jan. 12, 1983, discloses the preparation of p-phenoxybenzoyl compounds by reacting diphenyl ether and an appropriate acyl compound such as acetic anhydride in the presence of hydrogen fluoride.

Meussdoerffer et al, German Offenlegungsschrift No. 26 16 986 published Oct. 27, 1977 and assigned to Bayer AG, disclose the hydrogen fluoride-catalyzed acylation of phenolic compounds such as phenol itself with an acyl halide such as acetyl chloride to form hydroxy aromatic ketones.

SUMMARY OF THE INVENTION

In accordance with this invention, hydroxy aromatic ketones such as 4-hydroxyacetophenone (4-HAP) are produced by the Friedel-Crafts acylation of monocyclic phenolic reactants with substantially less than one mole of a carboxylic acid anhydride per mole of phenolic reactant. The reactions involved in the process as hereinafter described are carried out in the presence of any suitable Friedel-Crafts catalyst.

The anhydride initially added reacts with an equivalent of phenolic reactant to produce an equivalent of hydroxy aromatic ketone yielding a corresponding equivalent of free carboxylic acid as a by-product. Additional phenolic reactant then reacts with the liberated carboxylic acid in the same reactor to produce an additional amount of hydroxy aromatic ketone. If one half mole of anhydride per mole of phenolic compound is used, the result will be a balanced process with a theoretical yield of one mole of hydroxy aromatic ketone per mole of phenolic reactant. If a somewhat larger amount of anhydride is used than one half mole per mole of phenolic reactant, an excess of free carboxylic acid will be produced, while if somewhat less anhydride is used, not all the phenolic reactant will be used up in the reaction, i.e., some phenolic reactant will remain at the end of the reaction.

The two reactions of the process proceed in accordance with equations (I) and (II) as follows:

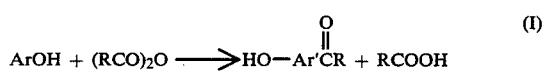

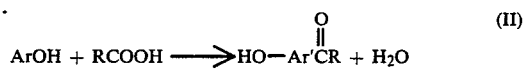

where Ar, Ar' and R are as defined hereinafter.

When it is desired to produce 4-HAP by the acetylation of phenol with acetic anhydride, the process proceeds as follows in accordance with equations (III) and (IV):

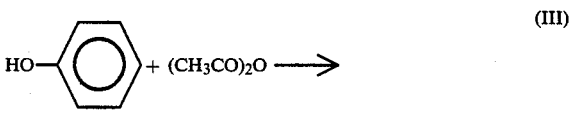

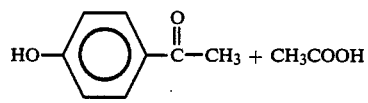

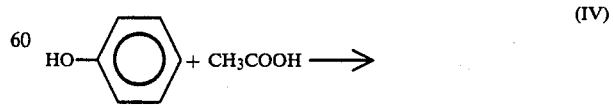

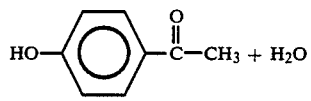

When one half mole of acid anhydride is employed per mole of phenolic reactant, the reactions of the overall process may be described as in equation (V):

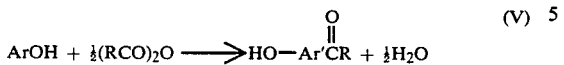

$$ArOH + \tfrac{1}{2}(RCO)_2O \longrightarrow HO-Ar'\overset{O}{\overset{\|}{C}}R + \tfrac{1}{2}H_2O \qquad (V)$$

In equations (I), (II) and (V), Ar is a monovalent monocyclic aromatic radical, preferably a phenyl radical, either unsubstituted or with ring hydrogens substituted with radicals such as alkyl, alkoxy or acyloxy containing 1 to 18 carbon atoms, halogen, e.g. chlorine, bromine, or iodine; and appropriately masked hydroxy, amino, or sulfhydryl. Ar is preferably phenyl or o-cresyl.

In the same equations, Ar' is a divalent monocyclic aromatic radical corresponding to the definition of Ar given previously except with an additional ring carbon atom replaced by a free valence. Ar' is preferably 1,4-phenylene or 3-methyl-1,4-phenylene with the ketocarbon occupying the first stated numbered position of Ar' when the positions are not equivalent. Most preferably Ar' is 1,4-phenylene.

The R groups in the foregoing equations are alkyl groups containing, for example 1 to 18 carbon atoms, preferably 1 to 4 carbon atoms. More preferably, R is methyl, ethyl or propyl and most preferably methyl corresponding to acetic anhydride, acetic acid and hydroxy aromatic methyl ketones in the equations.

Phenolic reactants which may be used, for example, are phenol and o-cresol; and acid anhydrides which may be used are acetic, propionic and n-butyric anhydrides. The preferred reactants are phenol and acetic anhydride and the preferred product is 4-hydroxyacetophenone (4-HAP).

The catalyst for both of the reactions of this invention is preferably hydrogen fluoride but any other catalyst known in the art to be effective for Friedel-Crafts reactions may be used, e.g. aluminum chloride, zinc chloride, or boron trifluoride.

Note that although the reaction of a phenolic compound and an acylating agent is characterized herein as a "Friedel-Crafts acylation", no opinion as to the mechanism of reaction should be implied by this characterization.

In carrying out the reaction so as to obtain particularly high yields of hydroxy aromatic ketone within this invention, the phenolic reactant is reacted, for example, with about 0.4 to 0.8 moles, preferably about 0.45 to 0.55 moles and most preferably about 0.5 mole, of acid anhydride per mole of phenol at a temperature of reaction, for example, of about 0° to 100° C., in the presence of a suitable catalyst for a reaction period, for example, of about 15 to 120 minutes, preferably about 30 to 75 minutes.

If HF is used as the catalyst it may be charged as a liquid or a gas using technologies of handling well-known to those skilled in the art. An excess of HF is generally used, for example, about 8 to 60 moles per mole of phenolic reactant intially present in the reaction zone. In general, the temperature of reaction when HF is employed as a catalyst will be in the range, for example, of about 30° to 95° C., preferably about 40° to 80° C.

Using a corrosion-resistant reactor, the reaction is initiated by either: (1) charging the catalyst to a mixture of phenolic reactant and acid anhydride at a temperature less than the specified reaction temperature; (2) charging acid anhydride to a solution of phenolic reactant and catalyst at reaction temperature; or (3) charging acid anhydride and phenolic reactant simultaneously to the catalyst at reaction temperature. Regardless of the method of initially mixing the anhydride, phenolic reactant and catalyst, the reaction is then adjusted to the specified reaction temperature for the specified reaction period. The catalyst may be charged in any conventional form using technologies of handling well known to those skilled in the art. In carrying out the reaction, an inert gas such as nitrogen may be used to keep the reaction space under the desired pressure, about 2.5 to about 500 psig. This has the effect of keeping sufficient HF in contact with the reacting liquid, if HF is used as the catalyst.

In general, the process of this invention results in a conversion of phenolic reactant, e.g. phenol, of at least about 80%, preferably at least about 90%, with a selectivity to hydroxy aromatic ketone, e.g., 4-hydroxyacetophenone (4-HAP), of at least about 70%,, preferably at least about 90%.

The process of this invention may result in economy of production as compared to processes utilizing on the order of one mole of anhydride or free carboxylic acid per mole of phenolic reactant as acylating agent since a considerably smaller quantity of anhydride is employed in this process than the quantity of anhydride or acid in the other processes. Moreover product purification is simpler using the process of this invention since considerably less than one mole of water per mole of phenolic reactant need be removed from the product whereas close to one mole of acetic acid or water must be removed when the process utilizes about one mole of anhydride or acid per mole of phenolic reactant. Such simpler purification also results in less HF loss, if HF is used as the catalyst.

DESCRIPTION OF SPECIFIC EMBODIMENT

The following example illustrates the process of this invention.

Example

A 300 cc Hastelloy C autoclave was charged with 18.8 g (0.2 mol) of phenol, pressurized with nitrogen to 100 psig., cooled to −20° C. using a carbon dioxide/isopropanol bath, and then evacuated to ca. 175 Torr. To the autoclave were added 10.2 g (0.1 mol) of acetic anhydride and the contents of the autoclave were cooled to −25° C. whereupon 160 g (8.0 mol) of hydrogen fluoride were added. The mixture was warmed to 80° C. and maintained at that temperature for one hour with stirring. The contents of the reactor were cooled to 40° C. and the hydrogen fluoride was then vented through a caustic scrubber for one hour while simultaneously using a nitrogen purge. The product of the reaction was extracted with 100 mL ethyl acetate, 50 mL of water were added and the pH of the resulting aqueous phase was adjusted to 7.0 using a solution of 45% potassium hydroxide. The aqueous phase was extracted with 50 mL of ethyl acetate (2×). The organic extracts were combined, rinsed with a saturated sodium chloride solution, and the solvent was removed on a rotary evaporator to yield a crystalline product. The reaction proceeded with 97.5% conversion of phenol and with the indicated selectivities to 4-hydroxyacetophenone (94.7%), 2-hydroxyacetophenone (4.6%), and 3-hydroxyacetophenone (0.1%).

I claim:

1. A process comprising acylating phenol with about 0.4 to 0.8 moles of a carboxylic acid anhydride as acylating agent per mole of phenol in the presence of a Friedel-Crafts catalyst consisting of hydrogen fluoride to produce a hydroxy aromatic ketone.

2. The process of claim 1 wherein said carboxylic acid anhydride consists of acetic anhydride, and said hydroxy aromatic ketone is 4-hydroxyacetophenone.

3. The process of claim 2 wherein said process is carried out in the presence of about 8 to 60 moles of hydrogen fluoride per mole of phenol as catalyst, at a temperature of reaction of about 30° to 95° C. for a reaction period of about 15 to 120 minutes.

4. The process of claim 3 wherein a phenol conversion of at least about 80% and a reaction selectivity to 4-hydroxyacetophenone of at least about 70%.

5. The process of claim 4 wherein about 0.45 to 0.55 moles of acetic anhydride per mole of phenol are employed.

6. The process of claim 5 wherein about 0.5 mole of acetic anhydride per mole of phenol is employed.

7. The process of claim 5 wherein the phenol conversion is at least about 90% and the selectivity to 4-hydroxyacetophenone is at least about 90%.

8. The process of claim 3 wherein said reaction period is about 30 to 75 minutes.

9. The process of claim 8 where said temperature of reaction is about 40° to 80° C.

* * * * *